United States Patent
Rosenblood et al.

(10) Patent No.: US 7,478,452 B2
(45) Date of Patent: Jan. 20, 2009

(54) TOOTHBRUSH HAVING A TONGUE SCRAPER

(75) Inventors: Kenneth Rosenblood, Los Angeles, CA (US); Christopher N. Quan, Quincy, MA (US)

(73) Assignee: Discus Dental, LLC, Culver City, CA (US)

( * ) Notice: Subject to any disclaimer, the term of this patent is extended or adjusted under 35 U.S.C. 154(b) by 59 days.

(21) Appl. No.: 11/417,024

(22) Filed: May 3, 2006

(65) Prior Publication Data

US 2006/0248668 A1    Nov. 9, 2006

Related U.S. Application Data

(60) Provisional application No. 60/677,532, filed on May 3, 2005.

(51) Int. Cl.
*A61B 17/24* (2006.01)
*A46B 15/00* (2006.01)
*A45D 44/18* (2006.01)

(52) U.S. Cl. .......................................... 15/111; 606/161
(58) Field of Classification Search .................. 15/111; 606/161
See application file for complete search history.

(56) References Cited

U.S. PATENT DOCUMENTS

| | | | | |
|---|---|---|---|---|
| 1,495,675 A * | 5/1924 | Colt | ............................ | 132/309 |
| 2,599,658 A * | 6/1952 | Perwas | ........................ | 401/178 |
| 4,610,043 A * | 9/1986 | Vezjak | .......................... | 15/111 |
| 5,005,246 A * | 4/1991 | Yen-Hui | ........................ | 15/111 |
| 5,133,102 A * | 7/1992 | Sakuma | ....................... | 15/167.1 |
| 5,282,814 A * | 2/1994 | Srivastava | ................... | 606/161 |
| 5,530,981 A * | 7/1996 | Chen | ............................. | 15/111 |
| D376,426 S * | 12/1996 | Tarfare et al. | ............... | D24/152 |
| 5,709,004 A * | 1/1998 | Paduano et al. | ................ | 15/111 |
| 5,737,792 A * | 4/1998 | Quigless | ..................... | 15/167.1 |
| 5,810,856 A * | 9/1998 | Tveras | ......................... | 606/161 |
| 5,845,358 A * | 12/1998 | Woloch | ........................ | 15/111 |
| 5,980,541 A * | 11/1999 | Tenzer | ......................... | 606/161 |
| 6,266,840 B1 * | 7/2001 | Munro | ......................... | 15/167.1 |
| 6,647,581 B1 * | 11/2003 | Persad et al. | ................... | 15/111 |
| 7,051,394 B2 | 5/2006 | Gavney | | |
| 2004/0134008 A1 * | 7/2004 | Pham | ........................... | 15/111 |
| 2004/0237995 A1 * | 12/2004 | Mualem et al. | ............. | 132/311 |

FOREIGN PATENT DOCUMENTS

| WO | WO 2006/055571 A2 | 5/2006 |
|---|---|---|
| WO | WO 2006/055572 A1 | 5/2006 |
| WO | WO 2006/055574 A2 | 5/2006 |

* cited by examiner

*Primary Examiner*—David B Thomas

(57) ABSTRACT

A dental apparatus includes a substantially longitudinal housing having a distal end, a proximal end having a tooth brush attached to it, and a tongue scraper attached to the housing. The tongue scraper can be attached to the inside or the outside of the housing. It can be fully extended during storage or in a roll form. The tooth brush can be an electric tooth brush. The tooth brush may also include a light source.

The housing may also include vents along a portion thereon so that the tongue scraper may be cleaned and air dried during storage. The tongue scraper may extend outwardly from the distal end of the housing, perpendicular to the housing, or in a manner resembling a bow.

36 Claims, 8 Drawing Sheets

TOOTHBRUSH HAVING A TONGUE SCRAPER

CROSS REFERENCE TO RELATED APPLICATIONS

This application claims the benefit of U.S. provisional patent applications: Ser. No. 60/677,532 entitled "Tooth-Brush" filed May 3, 2005.

FILED OF THE INVENTION

This invention relates broadly to improvements in the field of oral hygiene. Specifically, this invention relates to a dental apparatus for use in oral hygiene.

BACKGROUND OF THE INVENTION

The human tongue is not a smooth surface and has numerous protuberances, e.g., papillae, which convey to the brain the senses of taste and touch. However, due to the non-uniform surface of the tongue, it may also be a breeding ground for microorganisms such as bacteria and may retain food debris, volatile sulfur compounds (which may be a major cause of halitosis) and dead cells. Over time, some of the collected material becomes a soft plaque which may be another cause of bad breath and is also known to attack the teeth and gums. Tests have shown that daily scraping to reduce the amount of coating on the tongue may eliminate much of the undesirable bacteria and sulfur compounds, and thus may significantly inhibit plaque formation on the teeth in the long term, and substantially reduce halitosis in the short term.

A wide variety of tongue scrapers are known in the dental hygiene arts. For example, U.S. Pat. No. 3,477,435 to Artelli discloses a tongue scraper with a metal blade-like member having an end portion formed to fit between wooden handle parts. A rigid blade-like portion extends forwardly of the handle at the other end in a curve which is configured either for a right-handed person or for a left-handed person. U.S. Pat. No. 3,890,964 to Castanedo discloses a one-piece tongue scraper which includes an elongated handle at one end with longitudinally diverging arms at the other end. The ends of the arms are connected by a longitudinally bowed cross bar having a laterally centered, arched portion and beveled edge faces. U.S. Pat. No. 4,455,704 to Williams discloses a tongue cleaner in combination with a toothbrush. The tongue cleaner is an arcuate scraper member which is centrally secured to the tooth brush handle at the end opposite the brush. U.S. Pat. No. 5,217,475 to Kuber discloses a disposable tongue scraper which is intended to be used only once.

Combining toothbrushes and tongue cleaners is also known in the prior art. U.S. Pat. No. 5,842,247 issued Dec. 1, 1998 to Decesare discloses a combination tooth brush and tongue brush. U.S. Pat. No. Des. 377,417 issued Jan. 21, 1997 to Gupta, U.S. Pat. No. Des. 283,952 issued May 27, 1986 to Berkowitz and U.S. Pat. No. Des. 265,270 issued Jul. 6, 1982 to McCarty all disclose combined tooth brush and tongue cleaners. Each of these designs shows a handle portion having a tooth brush at one end and an exposed tongue cleaner fixed at an opposite end.

U.S. Patent Application 20040134008 discloses a tongue cleaner that takes the form of an elongated, linear, flexible strip disposed in a cavity of the tubular handle portion. The strip has a proximal end attached to a movable retainer and a distal end connected to a finger puller which normally closes the open end of the handle portion so that a finger puller is used to pull out the strip from the handle portion for tongue cleaning and push back the strip into the handle portion when tongue cleaning is complete.

While these prior art devices may fulfill their respective objectives, there still exists a need for a combined tooth brush and tongue scraper which may be utilized to remove plaque coating bacteria, reduce halitosis and lead to better overall mouth cleaning and oral hygiene.

SUMMARY OF THE INVENTION

The present invention relates to a dental apparatus having attached thereto a tooth brush and a tongue scraper which is exposed for use, appropriately stored when not in use, and if reuseable, may be cleaned and dried for subsequent use.

In one exemplary embodiment of the invention, a dental apparatus may include a substantially hollow housing having a distal end, a proximal end, and a tooth brush at its proximal end. The tooth brush portion may be permanently attached or it may be detachable and replaceable. A tongue scraper may be housed inside the substantially hollow housing during storage. The housing may include vents substantially along at least one side and may allow for air drying of the tongue scraper after cleaning to minimize or prevent any potential moisture accumulation which may result in microbial growth.

In one aspect, the tongue scraper may be slidably mounted and present in extended form inside the housing. The housing may include an opening at the distal end or along one side. With an opening at the distal end, the tongue scraper may be pulled out as an extension of the housing or in a perpendicular direction to the housing. With an opening along one side, the tongue scraper may be pulled out in a perpendicular direction, in an extended form or in a manner resembling drawing a bow. The opening may be fitted with a door and in the embodiments with doors, the vents discussed above may be present in the door or on the side of the housing.

In another aspect, the tongue scraper may be sufficiently flexible to be present in a roll during storage inside the housing. The roll may be of a sufficient length when extended to form at least one tongue scraper. When the opening is at the distal end, the tongue scraper may be pulled out as an extension of the housing, or perpendicular to the housing. After use, it may be retracted back into storage or in a disposable embodiment, it may be torn off and disposed of to reduce cross-contamination. When the opening is along one side, the tongue scraper may be pulled out in a perpendicular direction, in extended form or in a manner resembling drawing a bow. The opening may further be fitted with a door. The roll may be fixedly or slidably attached to the proximal end of the housing, anywhere inside the housing, or to the distal end of the housing.

In other aspects, the housing may include features that may remove or exclude moisture and/or particulates from the tongue scraper as it is being retracted into the housing. These features may include a projection or protrusion along the retraction path of the tongue scraper. The projection or protrusion may be absorbent as a means of removing moisture from the tongue scraper as it slides past. In other embodiments, the projection or protrusion may be a rubber-like material and may act in a manner similar to a windshield wiper or squeegee to remove moisture and particulates from the tongue scraper as it slides past.

In a further aspect, the housing may include features that may coat the tongue scraper as it is being pulled out of the housing with any therapeutic agent discussed below. These features may include a projection or protrusion along the path of the tongue scraper and may be means for carrying the agents noted from a reservoir or storage onto the tongue scraper.

In another exemplary embodiment of the invention, a dental apparatus may include a housing having a distal end, a proximal end, and a tooth brush at its proximal end. The housing may have a substantially hollow interior. The tooth brush portion may be permanently attached or it may be detachable and replaceable. The tooth brush may also be an electric tooth brush. The brittles may also be coated with a therapeutic agent, such as those used in coating the scraper, or others that may be beneficial to the tooth or teeth, as discussed in more detail below. In one embodiment, a tongue scraper may be present in a roll inside the substantially hollow housing during storage. The roll may be of a sufficient length when extended to form at least one tongue scraper. The housing may include an opening at the distal end or along one side. When the opening is at the distal end, the tongue scraper may be pulled out as an extension of the housing, or perpendicular to the housing. After use, it may be retracted back into storage or, in a disposable embodiment, it may be torn off and disposed of to reduce cross-contamination. When the opening is along one side, the tongue scraper may be pulled out in a perpendicular direction, in extended form or in a manner resembling drawing a bow. The opening may further be fitted with a door. The roll may be fixedly or slidably attached to the proximal end of the housing, anywhere inside the housing, or to the distal end of the housing.

In one aspect, as noted above, the housing may include vents substantially along at least one side or portion and may allow for air drying of the tongue scraper after cleaning to minimize or prevent any potential moisture accumulation which may result in microbial growth. In another aspect, the housing may also have vents at its distal end portion or in the door.

In other aspects, the housing may include features that may remove or exclude moisture and/or particulates from the tongue scraper as it is being retracted into the housing, as mentioned above.

In a further aspect, as also mentioned above, the housing may include features that may coat the tongue scraper as it is being pulled out of the housing with any therapeutic agent discussed below.

In another embodiment, the tongue scraper may be attached to the outside of the substantially longitudinal housing. An attachment may be fashioned to allow the tongue scraper to be swung outwardly, either as an extension of the housing or in a perpendicular direction for use, cleaned and then pushed back alongside the housing after use. In one aspect, the tongue scraper may be fixedly or slidably attached on both ends and the scraper may be pulled away from the outside of the housing in a manner resembling drawing a bow, ready to be use. In another aspect, one end of the scraper is fixedly or slidably attached to one end of the housing. The tongue scrapper may be in extended form or in a roll during storage. In still a further aspect, the tooth brush and tongue scrapper combination may also be housed inside a second housing and may be removed from the second housing for use. The second housing may also include vents to allow air-drying of both the tooth brush and tongue scraper after use.

In a further exemplary embodiment of the invention, a dental apparatus may include a housing having a door along a longitudinal portion of the housing. The tongue scraper may be extended or in a roll while residing inside the housing. In one aspect, the tongue scraper may be pulled out of the housing in a perpendicular direction, in extended form or in a manner resembling drawing a bow. The housing may have vents along at least one portion so that after each use and cleaning, any moisture on the tongue scraper may be removed by air drying before next use to prevent any potential microbial growth. The vents may be present in the door or in the housing. The housing may also have vents at its distal end portion.

In still a further exemplary embodiment of the invention, a dental apparatus may include a substantially hollow housing having two separate portions slidably attached to each other. In one aspect, the two portions may be joined in a manner such that when the two portions of the housing are pulled apart, the tongue scraper is exposed for use. In another aspect, the two separate portions may be telescopically fitted to each other so that when they are collapsed, the tongue scraper is stored inside the housing, and when they are extended, the tongue scraper is exposed for cleaning or use. The tongue scrapper may be fixedly or slidably mounted inside the housing. The tongue scraper may be extended or in a roll during storage. The housing may also have vents along at least a one side or at its distal end.

In one aspect, the outside of the tooth brush housing may be of an ergonomic design.

The tongue scraper may include a flexible material having two opposed generally planar end portions, and a generally planar central portion disposed between the two end portions. The strip of flexible material may also include two edges thereof. Each edge of the strip of flexible material may extend along the generally planar central portion between the two end portions.

In one embodiment, the tongue scraper may include at least one straight longitudinal edge. In another embodiment, the tongue scraper may include at least one serrated longitudinal edge. In a further embodiment, the tongue scraper may be a dual action tongue scraper including a comparatively hard scrape when the tongue scraper is bent one way, such that the tongue contacts a hard scraping surface which extends along one edge thereof; and a comparatively soft scrape when the tongue scraper is bent another way, such that the tongue contacts a soft scraping surface which extends along either the same or a different edge thereof. The hard scrape is generally more effective at removing the undesirable coating from the tongue, but the hard scrape may be too harsh for some people.

In one aspect, when the dual action tongue scraper is formed upon a common edge, the hard scraping surface and the soft scraping surface are separated by a generally flat portion of the common edge, so as to facilitate scraping of the tongue with only the desired one of the hard scraping surface and the soft scraping surface. In another aspect, one or both of the two edges may include a hard scraping surface and/or a soft scraping surface, if desired. In a further aspect, each of the two edges may either be configured as a smooth edge or a serrated edge, if desired. Further, in yet another aspect, each of the two edges may include either a substantially straight edge or a convex edge, if desired.

In some embodiments, the tongue scraper may include various coatings or treatments to further its cleaning function, to retard the growth of microbial contamination on the surface or to reduce its sensitivity. Coatings or treatments may be deposited on the surface of the tongue scraper by a variety of methods. Also, some treatments may be attached in a permanent fashion, such as by covalent linkage, such that the tongue scraper may have persistent activity.

As noted above, the coatings may also be present on the brittles of the brush portion, also for the same or similar therapeutic effects.

Any of the above described apparatuses may also be fitted with a light source. The light source may also have therapeutic effects or may be adapted for enhancing therapeutic effects of the coatings.

Other variations and equivalent structures of the present invention are also contemplated to be within the scope of the present invention.

BRIEF DESCRIPTION OF THE FIGURES

FIG. 1a(1) depicts a cross-sectional view of an embodiment of a dental apparatus of the present invention with a tongue scraper in a roll towards the proximal end of the housing;

FIG. 1b(1) depicts a cross-sectional view of an embodiment of a tongue scraper being pulled out in a perpendicular direction to the housing;

DETAILED DESCRIPTION OF THE INVENTION

The detailed description set forth below is intended as a description of the presently exemplified device provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein may be used in the practice or testing of the invention, the exemplified methods, devices and materials are now described.

Figure 1:
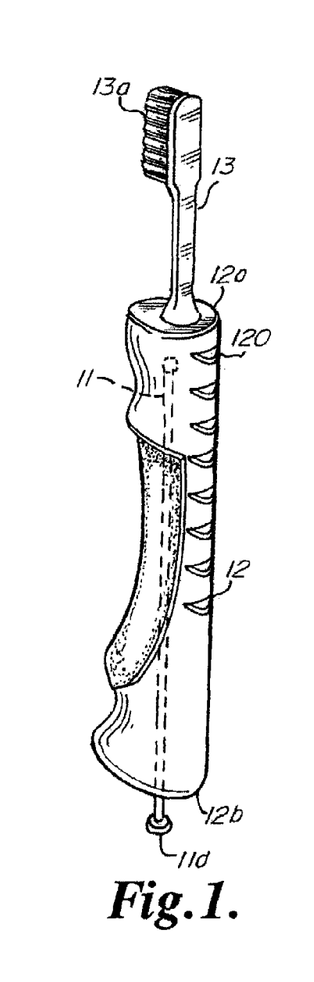
FIG. 1 depicts a side view of an embodiment of a tooth brush of the present invention.
Figure 1A:
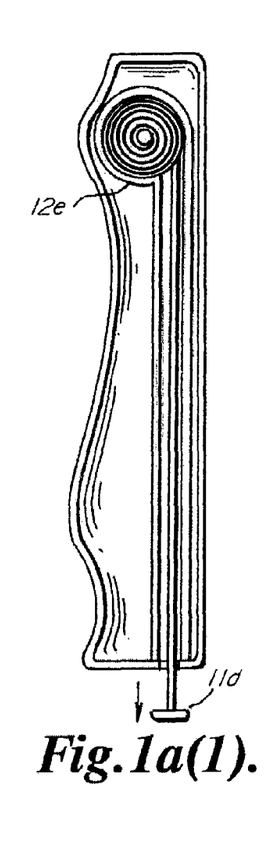
FIG. 1a depicts a cross-sectional view of an embodiment of a dental apparatus of the present invention.

The present invention relates to a dental apparatus 10 having a substantially elongated housing 12 with an interior 12c, a proximal end 12a, a distal end 12b, and a tongue scraper 11 disposed within the interior 12c of the housing 12, as exemplified in the embodiments in FIGS. 1 and 1a. A tooth brush portion 13 (as exemplified in FIGS. 1, 4 and 4a) may extend linearly outwardly from the proximal end 12a, and may have a plurality of upstanding bristles 13a thereon. The housing 12 may have vents 120 in at least a portion of the housing, so that after each use and cleaning, any moisture may be removed by air drying before the next use to prevent any potential microbial growth. The housing 12 may also have vents at its distal end.

As shown in FIG. 1, the tongue scraper 11 may be slidably mounted inside the housing 12. The housing 12 may include an opening 120a at the distal end 12b or along one side. When the opening is at the distal end 12b, the tongue scraper 11 may be pulled out as an extension of the housing, as exemplified in FIG. 1a, or perpendicular to the housing, as exemplified in FIG. 1b(1). When the opening 120a is along one side of the housing, the tongue scraper 11 may be pulled out in a perpendicular direction to the housing 12, fully extended, as exemplified in FIG. 2b, or in a manner resembling a bow, as exemplified in FIGS. 2 and 2a. The opening 120a may be fitted with a door 120b. In these embodiments, the vents discussed above may be present in the door 120b or in the side of the housing 12.

According to the embodiment exemplified in FIG. 1, the tongue scraper may be in fully extended form inside the housing 12, or the tongue scraper 11 may be sufficiently flexible to be capable of being wound into a roll 15 for storage inside the housing 12, as exemplified in FIGS. 1a, 1a(1) and 1b. The roll 15 may be of a sufficient length when extended to form at least one tongue scraper 11. The tongue scraper 11 may be pulled out in the same manner as discussed above, and may be retracted back into storage inside the housing after use. In another embodiment, the tongue scraper 11 or a portion of the tongue scraper 11 may be torn off and disposed of after use.

In one embodiment, the roll 15 may extend to form more than one tongue scraper 11. The length may be perforated to dispense one tongue scraper 11 at a time. Each length of a tongue scraper 11 may be torn off the roll along a perforation or a scored line 40 formed in a transverse direction, as exemplified in FIG. 9. In another embodiment, the roll 15 may extend to the useable length of only one tongue scraper 11, and therefore is only in a roll form during storage. In the exemplified embodiment of FIG. 1c, a single length tongue scraper 11 may be or may not be in a roll form 15. If not in a roll form, it may be fully extended inside the housing 12, as noted before and similar to the embodiment as exemplified in FIG. 1c, except that the roll 15 serves as one embodiment of an attachment or a movable retainer for the tongue scraper 11. The roll 15 may be adapted to run along the track 122.

In the embodiment of FIG. 1a, the roll 15 may be mounted anywhere along the length of the interior of the housing 12. In another embodiment, the roll 15 may be mounted towards the distal end 12b of the housing 12, as exemplified in FIG. 1b. In yet another embodiment, the roll 15 may be disposed towards the proximal end 12a of the housing 12, as exemplified in FIG. 1a(1). The mounting may be slidable or fixed.

Figure 4:
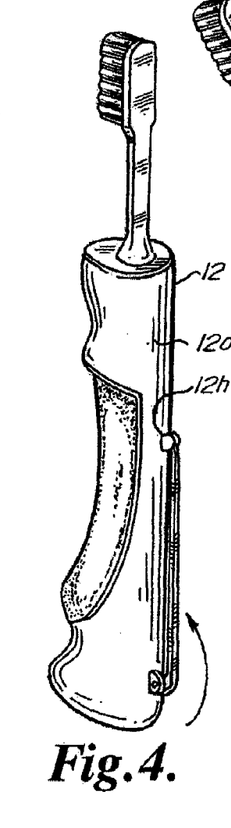
FIG. 4 depicts a perspective view of a dental apparatus of the present invention having a tongue scraper along the outside of the housing.
Figure 4A:
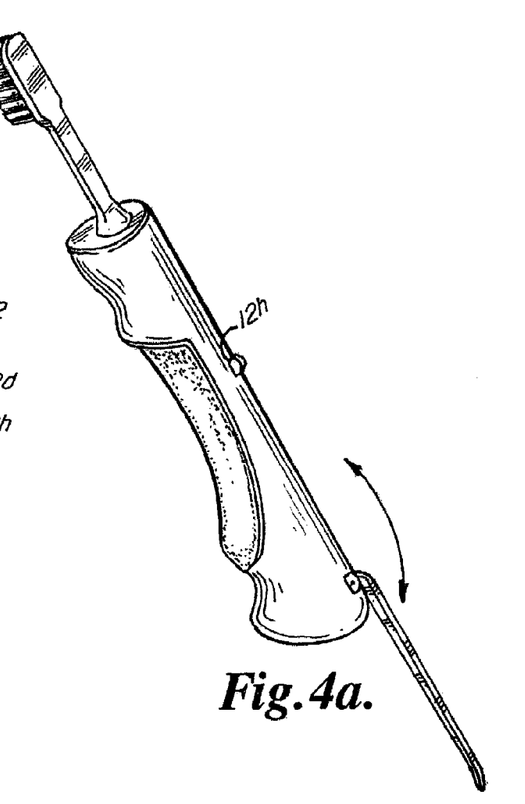
FIG. 4a depicts a perspective view of a dental apparatus of FIG. 4 having a tongue scraper along the outside of the housing attached at both ends.
Figure 5:
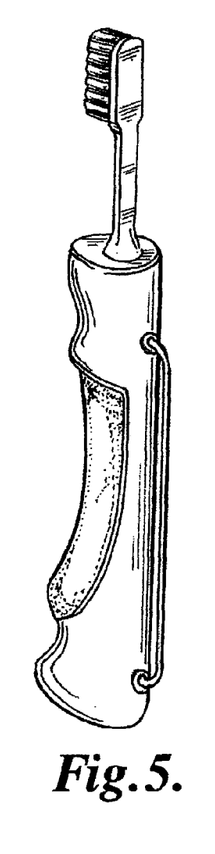
FIG. 5 depicts a perspective view of a dental apparatus of the present invention having a tongue scraper along the outside of the housing slidable attached at both ends.

In one embodiment, the tongue scraper 11 may be disposed along the exterior 12d of the housing portion 12, as exemplified in FIGS. 4 and 4a, for convenient storage when not in use, and for easy accessibility. The housing 12 may or may not have a substantially hollow interior, and may or may not have vents. The attachment may be made to allow the tongue scraper 11 to be swung outwardly, either as an extension of the housing 12, as exemplified in FIG. 4, or in a perpendicular direction (not specifically shown), for use, cleaned and then pushed back along the housing 12 12 after use. In one aspect, the tongue scraper 11 may be fixedly attached at one end of the housing, as exemplified in FIG. 4, with a retaining point 12h, as exemplified in FIGS. 4 and 4a. In another aspect, the tongue scraper 11 may be slidably attached on both ends, as exemplified in FIG. 5, and may be pulled away from the outside of the housing 12 in a manner resembling a bow, as exemplified in FIG. 5a, ready to be use. The tongue scraper 11 may be extended or in a roll 15 during storage. In a further aspect, the dental apparatus may also be housed inside a second housing 30 during storage, as exemplified in FIG. 6. The second housing 30 may also include vents 30a.

Figure 3:
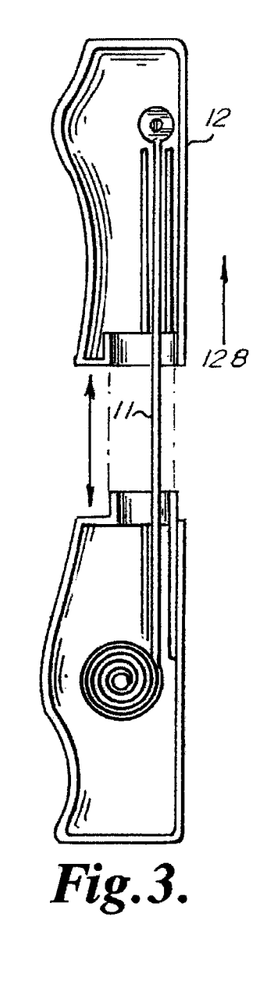
FIG. 3 depicts a cross-sectional view of an embodiment of the invention having a housing with two separate portions detachably joined to each other with a tongue scraper inside.
Figure 3A:
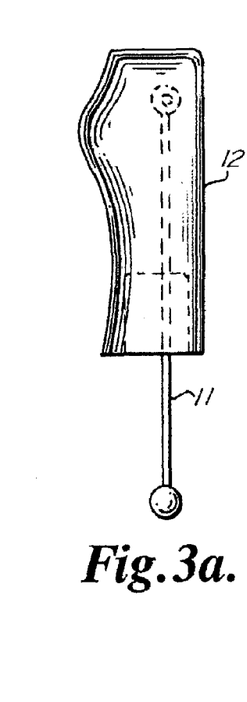
FIG. 3a depicts a perspective view of an embodiment of the present invention having a housing with two separate portions telescopically attached to each other.

In another exemplary embodiment, the housing 12 of the dental apparatus may be in two separate portions, slidably joined to each other, as exemplified in FIGS. 3 and 3a. As shown in FIG. 3, a tongue scarper 11 may be housed in the interior 12c of the housing 12. When the two portions of the housing 12 are pulled apart, the tongue scraper 11 may be exposed for use. In one aspect, the tongue scrapper 11 may be extended and may be slidably mounted inside the housing 12. In another aspect, the tongue scrapper 11 is substantially flexible and is wound into a roll 15 which may be fixedly or slidably mounted inside the housing 12.

Figure 2:
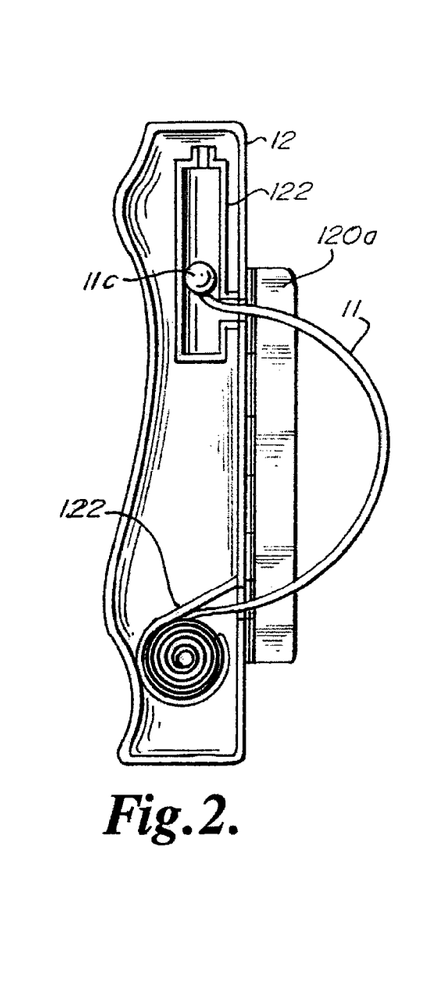
FIG. 2 depicts a cross-sectional view of a dental apparatus of the present invention having a housing with an opening along one side fitted with a door.
Figures 13A, 13B:
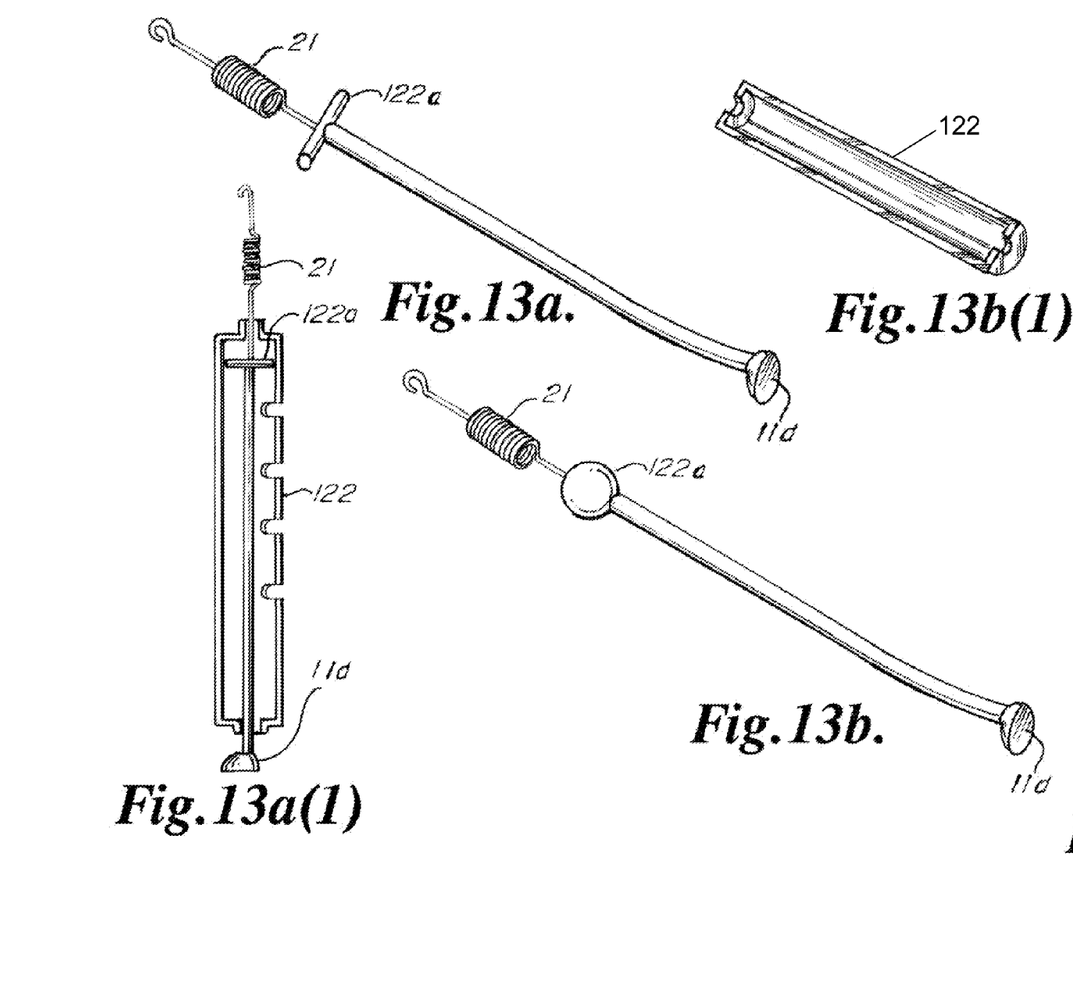
FIGS. 13a and 13a(1) depict a tongue scraper having a transverse post extending from an end and its corresponding track inside the housing.
FIGS. 13b, 13b(1) and 13b(2) depict a tongue scraper having a bead-like protrusion towards one end and a corresponding track inside the housing.
Figure 13B:
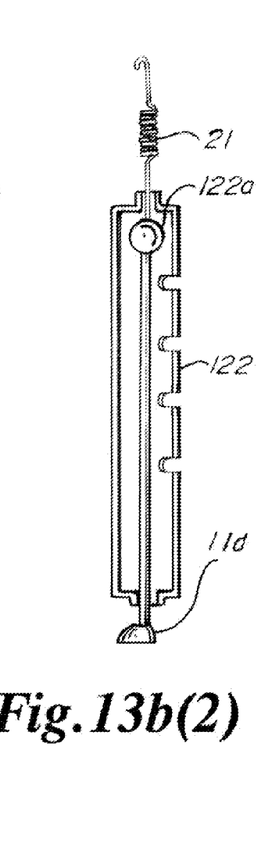

In the embodiment as shown in FIG. 3, one housing portion may include a lip portion 12g, or similar structure, at one end to be fitted over an indentation 12f, or similar structure, of a corresponding end of the second housing portion. The housing may include a track, as exemplified in FIG. 3 and similar to those disclosed in FIGS. 2 and 13a. Each end of a tongue scraper 11 may be slidably attached to a respective housing portion, and may slide along the track. The corresponding attachment points are as shown in FIGS. 2, 13a and 13b. During storage, the ends of the tongue scraper 11 are resting towards the end portions of the housing 12. This track arrangement may also be used in the embodiment exemplified in FIG. 3a. In another embodiment, the track of FIG. 3 may include a telescopic post or similar, not specifically shown, for easy expansion and retraction during separation and mating of the two portions of the housing 12.

In FIG. 3a, the two separate portions of the housing 12 may be of different sizes so that they can be telescopically mated, one portion inside the other portion, such that when the two portions are extended, the tongue scraper 11 is stored inside the housing 12, and when the two portions of the housing are collapsed together, the tongue scraper 11 is exposed for use. The housing 12 may be, for example, longer than a usual tooth brush handle so as to accommodate a full length tongue scraper 11 when the two portions are collapsed together. This arrangement may also allow a previously used portion of the tongue scraper 11 to be dried more thoroughly during storage. As with other embodiments described herein, the housing 12 may also have vents 120 to facilitate drying.

In one aspect, the tongue scrapper 11 in the embodiments of 3 and 3a may be extended during storage and fixedly or slidably mounted inside the housing 12. In another aspect, the tongue scrapper 11 may be substantially flexible and may be wound into a roll 15 inside the housing 12.

When in a roll form, the tongue scraper 11 in any of the above disclosed embodiment, for example, may be not too tightly wound, so as to facilitate the drying process. The vent hole 120 may also extend the length of at least one side of the housing, as shown in FIG. 2. A flexible material, though not too flexible may be used for the not so tightly wound up version.

Figure 1B:
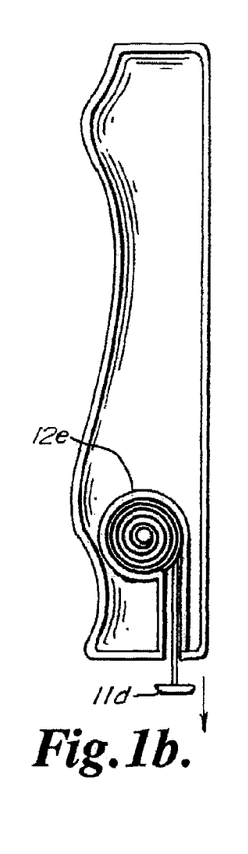
FIG. 1b depicts a cross-sectional view of a dental apparatus of the present invention with a tongue scraper in a roll attach towards the distal end of the housing.

In some embodiments, the housing 12 may include features 17 that may remove or exclude moisture and/or particulates from the tongue scraper 11 as it is being retracted into the housing 12. As shown in FIG. 1e, the features 17 may include projections or protrusions 17 along the retraction path of the tongue scraper 11. The projections or protrusions 17 may be of any absorbent material so as to function as a means of removing moisture from the tongue scraper as it slides past. The absorbent material may be an absorbent layer, a foam material, or a sponge. In other embodiments, the projections or protrusions 17 may be a rubber-like material and may act in a manner similar to a windshield wiper or squeegee to remove moisture and particulates from the tongue scraper 11 as it slides past.

In another embodiment, these features 17 may also be adapted for delivering a coating of therapeutic agents discussed in more detail below, onto the tongue scraper 11. The features 17 may be in the form brushes or tubes, acting as a conduit for delivery. The therapeutic agents may be stored in a reservoir inside the housing 12.

Figure 2A:
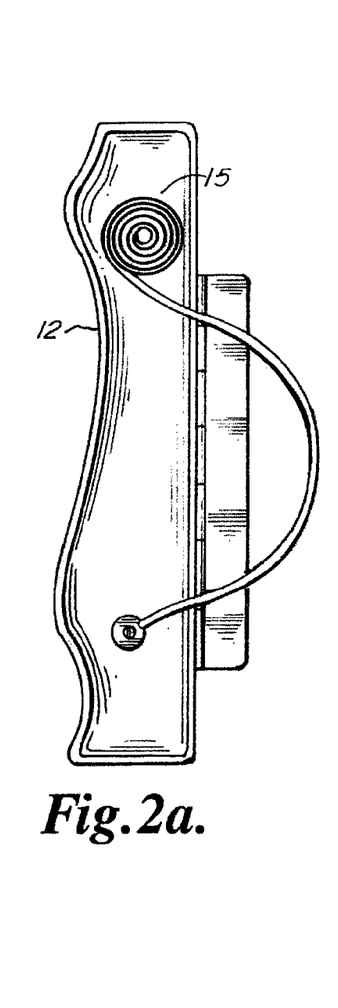
FIG. 2a depicts another embodiment of a cross-sectional view of a dental apparatus of the present invention having a housing with an opening along one side fitted with a door.
Figure 2B:
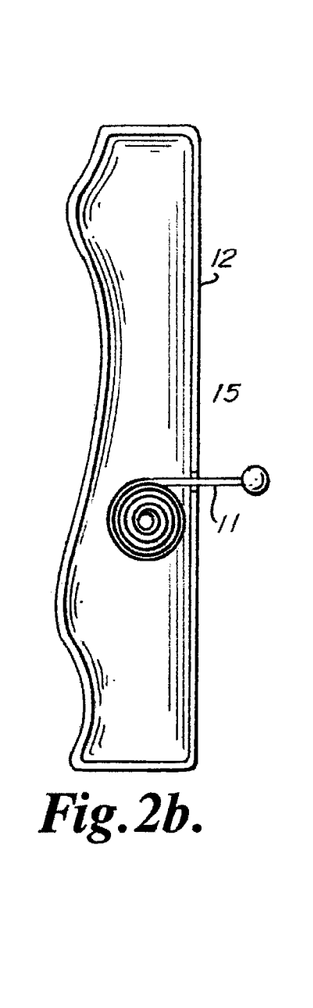
FIG. 2b depicts an embodiment of a cross-sectional view of a dental apparatus of the present invention having a housing with an opening along one side fitted with a door.

In FIGS. 2, 2a and 2b, the door 120b may be attached to the housing via hinges, or it may be integrally formed as part of the housing 12. When integrally formed, the opening and closing may be accomplished by a scored line around the opening 120a.

In one embodiment, the tongue scraper 11 may be manually pushed back inside the housing 12 or alongside the housing 12. In another embodiment, a mechanism may be provided so that the scraper 11 may be fully retracted automatically after use, such as the mechanisms used, for example, in a typical retractable tape rule assembly. Some of these mechanisms are described in, for example, U.S. Pat. Nos. 4,077,128; 4,215,828; 4,434,952; 4,578,867; 4,982,910 and 6,804,899, the contents of all of these are incorporated herein by reference.

Figure 1C:
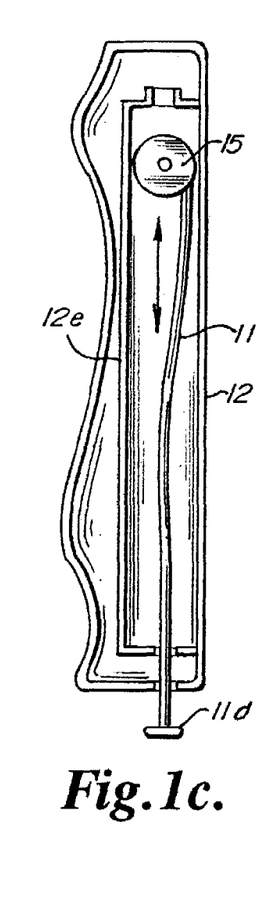
FIG. 1c depicts a cross-sectional view of a dental apparatus of the present invention with a tongue scraper in a roll slidably or fixedly attached to the housing.
Figures 1D, 1E:
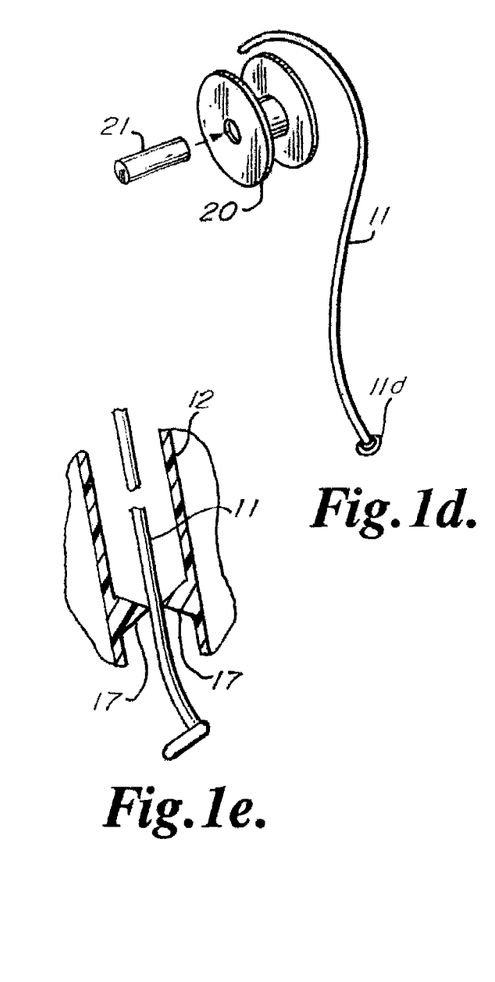
FIG. 1d depicts an exploded view of a roll of tongue scraper wound around a reel for rotatably disposed within the housing.
FIG. 1e depicts a partial cross-sectional view of a dental apparatus of the present invention with a tongue scraper and drying features attached to the housing.

In one embodiment, the inside surface of the housing 12 may include at least one channel or track 12e, as exemplified in FIG. 1c, for rotatably mounting an extended tongue scraper 11 or a roll 15. In another embodiment, the channel or track may be formed as a module to be mounted inside the housing 12, as exemplified in FIGS. 1c, 13a and 13b, and the tongue scraper 11 may be slidably mounted on the channel or track 122. In a further embodiment, the tongue scraper 11 may be present in a roll 15, fixedly or slidably mounted inside the housing 12 towards one end of the housing 12, as exemplified in FIG. 2a. In another aspect, the ends of the tongue scraper 11 may be wound into a roll (not shown) and fixedly mounted to the housing 12 on both ends.

Figure 11:
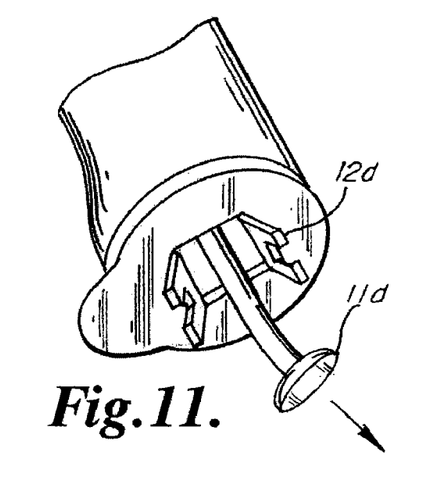
FIGS. 11 and 11a depict a trapping mechanism at the opening at the proximal end to keep the tongue scraper from retreating completely inside the housing.
Figure 11A:
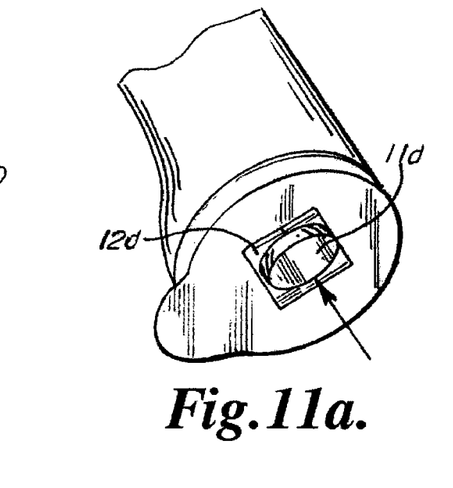

FIG. 1d shows an exploded view of a roll 15 of tongue scraper strip 11 mounted on a reel 20, which may in turn be rotatably or fixedly disposed within the housing 12. In one embodiment, the strip 11 may be retracted into the housing 12 for storage by coiling or winding it about the reel 20. In another embodiment, the reel 20 may include a spring loaded device for automatically coiling or winding the tongue scraper 11 about the reel 20 (not shown in FIG. 1d), as noted above. The spring loaded device may also include a locking mechanism so that the strip 11 may be locked in position when a sufficient length of the strip 11 is unwound for use. In a further embodiment, a braking mechanism such as a trap door 12d may be present at the distal end 12b of the housing 12 that may swing outwardly to allow the tongue scraper 11 to pass through, but does not allow an enlarged portion or gripping portion it to retract back into the housing 12, as shown in FIG. 11.

Figure 13C:
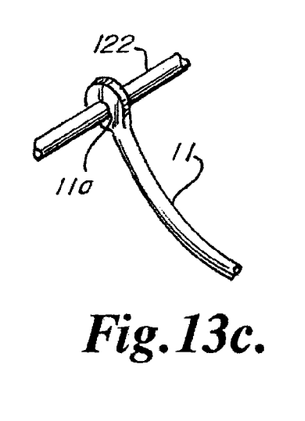
FIG. 13c depicts an embodiment of an attachment mode of the tongue scrapper to the track.
Figure 13D:
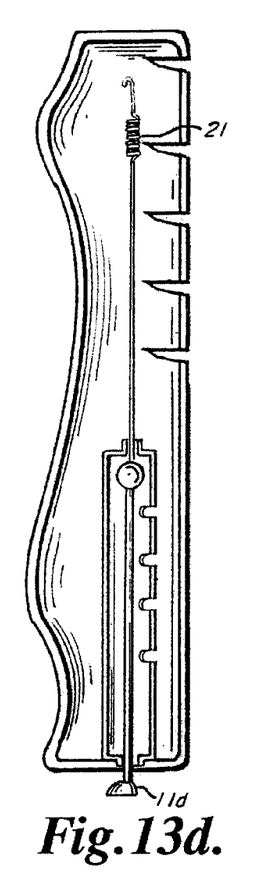
FIG. 13d depicts a cross-sectional view of an embodiment of a tongue scrapper inside the housing.

In one embodiment, a coil spring 21 may be mounted between the tongue scraper 11 and the inside of the housing 12, as exemplified in FIGS. 13a, 13b and 13d, so that the tongue scraper may be pulled out of the distal end 12b, as exemplified in FIGS. 1a, 1a(1), 1b, 1b(1), 1c, 13d and 11, or the opening doorway as exemplified in FIGS. 2, 2a and 2b, by extending the spring.

Figure 8:
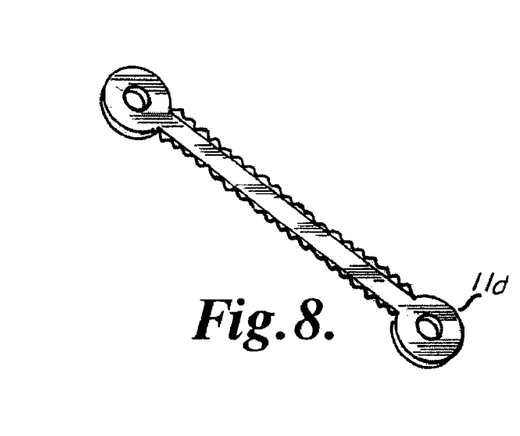
FIG. 8 depicts a dual action tongue scraper.
Figure 12:
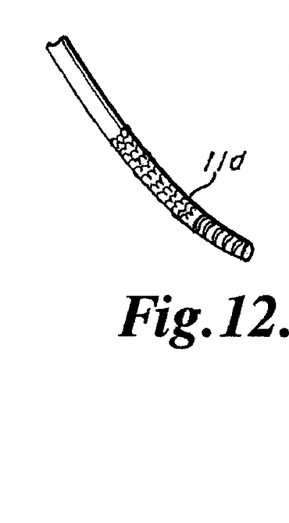
FIG. 12 depicts a tongue scraper having bumps, protrusions or roughened surfaces towards one end for ease of grasping.
Figure 12A:
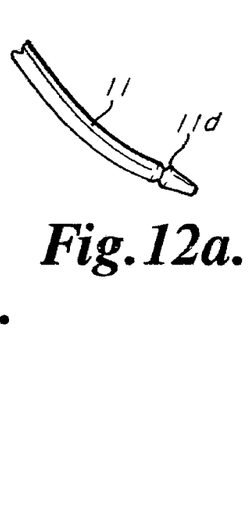
FIG. 12a depicts a tongue scraper having slots along its edge towards one end of the strip.

In one aspect, the tongue scraper 11 may be formed with a gripping device, or enlarge portion 11d, which may be in the form of a bead, a bar, or a paddle, as exemplified in FIGS. 1a, 1a(1), 1b, 1b(1), 1c, 1d, 2, 2a, 2b, 11 and 11a. The gripping device or enlarged portion 11d may also include a hole or a pull ring at an end portion allows the user to firmly grip the end portion to pull the tongue scraper 11 from its position of storage, as exemplified in FIGS. 8 and 10, or a slot 12d, as exemplified in FIG. 12a, for fitting in the trap door 12d. Further, the end portion of the tongue scraper 11 may also have a roughen surface with bumps or protrusions to facilitate gripping, as shown in FIG. 12.

In the embodiment as shown in FIG. 1a, the roll 15 is shown to be releasably attached to the housing 12 towards the distal end of the housing 12 by means of a post 21, as exemplified in FIG. 13a, which may slide along a channel 12e, as exemplified in FIGS. 1a(1), and 1c.

In the embodiment as shown in FIG. 1b, the channel 12e appeared towards the proximal end 12b, for mounting a roll 15. In the embodiment as shown in FIG. 1c, the channel 12e forms a sliding track to enable the tongue scraper 11 or a roll 15 to slide across the interior of the housing 12.

When the interior of the housing 12 includes a track 122, a tongue scraper 11 may be pulled out of the housing 12 along the track 122 during use. The tongue scraper 11 may include an attachment point at each end. The attachment point may include a hole, a protrusion or a post to be mated with the corresponding track 122. In one example, the attachment point to the track 122 may include a hole 11a towards one end of a tongue scraper 11, as shown in FIG. 13c. In another example, the tongue scraper 11 includes a post 122a extending substantially transversely from one end and is adapted to run along the track 122, as shown in FIG. 13a. The corresponding track 122 running substantially the length of the interior 12c of the housing 12, also, as shown in FIG. 2a, may accommodate a bead-like protrusion 11c or the like, towards one end of the tongue scraper, as shown in FIG. 2b.

Figures 5A, 6, 7, 7A:
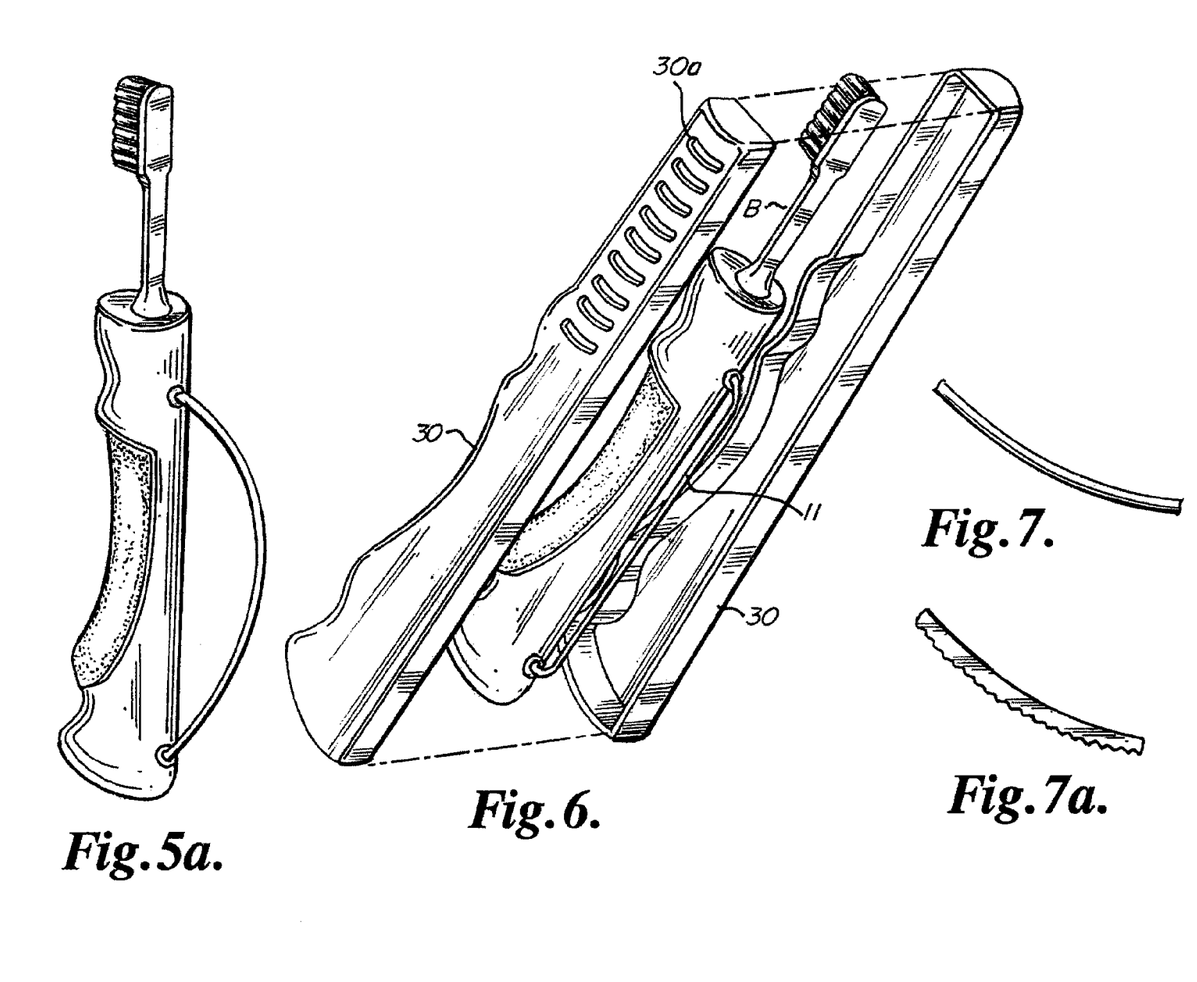
FIG. 5a depicts a perspective view of a dental apparatus of FIG. 5 having a tongue scraper along the outside of the housing slidable attached at both ends.
FIG. 6 depicts an exploded view of a dental apparatus of the present invention stored inside a second housing.
FIG. 7 depicts an embodiment of a tongue scraper made of a flexible strip having a straight edge.
FIG. 7a depicts an embodiment of a tongue scraper made of a flexible strip having a serrated edge)

When the tongue scraper 11 is attached along the outside of the housing 12, in the embodiment, as shown in FIG. 4, it may be attached towards one end of the housing 12, by means of any attachment means, such as a bolt, a nail, or similar, so long as the attachment allows the tongue scraper 11 to be swung away from the housing 12, as shown in FIG. 4a. In another embodiment, both ends of the scraper 11 may also be attached to both ends of the housing 12, which includes an internal sliding mechanism that may include any of the sliding means disclosed above or known in the art. In FIG. 5a, the tongue scraper 11 is ready for use and is pulled out in a manner resembling a bow, ready to be used.

If desired, any of the embodiments of the dental apparatus 10 may be stored inside a second housing 30, and one of them is shown in FIG. 6.

The brush portion 13 may be permanently or removably attached to the tooth brush 10. The removability may be effect by any known attachment methods. In addition, the tooth brush may also be an electric one including a vibrating tooth brush, and/or fitted with a light source. The light source may also be effective in promoting good oral hygiene. The light source may be, for example, any light emitting element such as an LED or an LED array. An example of a lighted tooth brush is disclosed in U.S. Pat. No. 6,752,627, the content of which is incorporated herein by reference. The light emitted may be effective in whitening and/or sterilizing.

Figure 9:
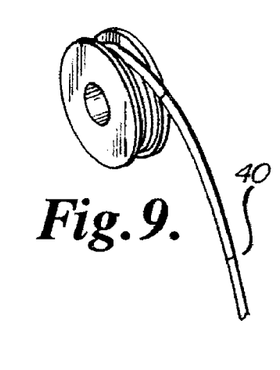
FIG. 9 depicts a roll of tongue scraper strips w/perforations.

As shown in the above, the tongue scraper strip 11, especially if present in a roll 15, may include more than one tongue scraper 11. The individual tongue scraper 11 may be separated along the perforations 40, as shown in FIG. 9. The perforations may be formed during the process of manufacturing, by scoring or hole punching, or by controlled depth die cutting after manufacturing.

The housing 12 may be of a substantially cylindrical shape, or has a substantially rectangular cross-section, or of a varying shape along its length. In some embodiments, the housing 12 may be of or an irregular or ergonomic shape, for example, having a thicker mid-section that tapers towards one or both ends ergonomic design for grasping, or similar to those exemplified in FIGS. 4, 4a, 5 and 5a.

The housing 12 may be made of any material including a polymer, a polymeric alloy, a filled polymer or alloy, a metal, a metallic alloy, and combinations thereof, as long as the housing 12 is relatively stiff.

Suitable polymers include polyethylene, polypropylene, polybutylene, polystyrene, polyester, acrylic polymers, polyvinylchloride, polyamide, or polyetherimide like ULTEM®; a polymeric alloy such as Xenoy® resin, which is a composite of polycarbonate and polybutyleneterephthalate or Lexan® plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used for the housing 101a.

Suitable metal or metallic alloys may include stainless steel or aluminum.

Suitable material for the tongue scraper 11 may include any flexible polymeric material, for example, polyethylene, polypropylene, polyester, polystyrene, acrylic copolymers, and so on.

The tongue scraper 11 may be constructed with two opposed generally planar end portions, and a generally planar central portion disposed between the two end portions. The strip of flexible material may also include two edges thereof. Each edge of the strip of flexible material extends along the generally planar central portion between the two end portions. The detailed construction is found in U.S. Pat. Nos. 5,868,769; 6,383,202; 6,428,554 and 6,451,038, the entire contents of which are incorporated herein by reference.

In one embodiment, the tongue scraper 11 may include at least one straight longitudinal edge, as shown in FIG. 7. In another embodiment, the tongue scraper 11 includes at least one serrated longitudinal edge, as exemplified in FIG. 7a. In a further embodiment, the tongue scraper 11 may be a dual action tongue scraper 11, as exemplified in FIG. 8, and may include a comparatively hard scrape when the tongue scraper 11 is bent one way, such that the tongue contacts a hard scraping surface which extends along one edge thereof; and a comparatively soft scrape when the tongue scraper 11 is bent another way, such that the tongue contacts a soft scraping surface which extends along either the same or a different edge thereof. The hard scrape is generally more effective at removing the undesirable coating from the tongue, but the hard scrape may be too harsh for some people.

In one aspect, when the dual action tongue scraper 11 is formed upon a common edge, the hard scraping surface and the soft scraping surface are separated by a generally flat portion of the common edge, so as to facilitate scraping of the tongue with only the desired one of the hard scraping surface and the soft scraping surface. Some of these designs are also described in U.S. Pat. Nos. 5,868,769; 6,383,202; 6,428,554 and 6,451,038, the entire contents of which are incorporated herein by reference.

In another aspect, one or both of the two edges may include a hard scraping surface and/or a soft scraping surface, if desired. The hard or soft scraping surfaces can take the design of those disclosed in U.S. Pat. Nos. 5,868,769; 6,383,202; 6,428,554 and 6,451,038, the entire contents of which are incorporated herein by reference.

In a further aspect, each of the two edges may either be configured as a smooth edge or a serrated edge, if desired.

Further, in yet another aspect, each of the two edges may include either a substantially straight edge or a convex edge, if desired.

Figure 10:
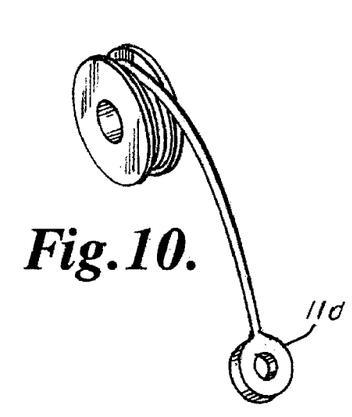
FIG. 10 depicts a roll of tongue scrapers having a pull-ring.

As discussed above, the tongue scraper, including the dual action tongue scraper 11, may be in roll form, as exemplified in FIGS. 9 and 10, having perforations or scored lines 40 to facilitate separation.

In some embodiments, the tongue scraper 11 may include various coatings and/or treatments that may facilitate its cleaning functions, application of a medicament, and/or help maintain sterility during use and storage. For example, the tongue scraper 11 may be coated with an antimicrobial composition. Antimicrobial agents may be employed to retard or kill microbes on the tongue scraper 11 and the tongue by contact and/or deposition of the agent on the tongue. These antimicrobial agents may help to get rid of, prevent or diminish bad breath, or symptoms of bad oral health. Atimicrobial agents may include, but are not limited to, antibiotics such as β-lactams (e.g. penicillin), aminoglycosides (e.g. streptomycin) and tetracylcines (e.g. doxycycline), antimycotics such as polyene drugs (e.g. amphotericin B) and imidazole and triazole drugs (e.g. fluconazole), and general antimicrobial agents such as quaternary ammonium cations (e.g. benzalkonium chloride or cetylpyridinium chlrodide (CPC)) and compounds such as triclosan and chlorhexidine. The composition may include a binding agent, an antimicrobial agent and/or other materials conducive to its retention on the tongue scraper and its use as a sterilizing agent. Suitable binding agents may include, but are not limited to, polymers such as polyethylene oxide (PEO), polylactic acid (PLA) and polyglycolic acid (PGA), polysaccharides such as carrageenan, chondroitin sulfate, ethylcellulose, hydroxypropylcellulose, carboxymethylcellulose, hydroxypropylmethylcellulose and polyvinylpyrrolidone. Other materials in the coating may include flavorants, including sweeteners such as various sugar alcohols (e.g. xylitol), artificial sweeteners (e.g. aspartame) and artificial flavors (e.g. vanillin).

In some embodiments, an antimicrobial coating or a coating of a medicament may be included that may dissolve on contact with the moist tongue, thus allowing dispersal of the antimicrobial agent or medicament. Water soluble carriers such as hydroxypropylcellulose, polyvinylpyrrolidone or carrageenan may be employed to effect such action. In other embodiments, the antimicrobial agent or medicament may be retained in an insoluble carrier that may linger on the tongue and slowly release the therapeutic. The medicament may include any medicine that may be effective when slowly dissolves or releases. Insoluble high molecular weight carriers, such as PEO, or biodegradable carriers, such as PLA and PGA, may be employed to effect such action.

In other embodiments, to increase the coating efficiency, the surfaces to be coated may be roughened or pitted.

In further embodiments, antimicrobial activity may be built into the tongue scraper itself by, for example, covalently bonding antimicrobial agents to the surface of the tongue scraper. These covalently bonded materials may act to minimize microbial growth on the tongue scraper 11, either disposable or reusable. In addition, any microbial organisms that may chance to be attached to the material may be killed by interaction with the coating. For example, quaternary ammonium cations, such as N-alkyl-pyridiniums, may be used as antimicrobial moeties in covalently attached polymeric surface coatings. In one case, poly(4-vinyl-N-hexylpyridinium) (N-alkylated-PVP) was previously noted to have an optimum alkyl side chain length for antimicrobial activity. The side chain length of the alkyl group may, for example, vary from 0 (to side chain) to 12 carbons long, more for example from 5 to 7 carbons long. The alkyl side chains may provide increased hydrophobicity for the coating and may promote association with microbial membranes. Polyethylenimine (PEI) was also previously used as a bacteriocidal coating when both N-alkylated on its primary amino group and subsequently N-methylated on its secondary and tertiary amino groups to raise the overall number of cationic quaternary amino groups. An increased number of cationic groups (permanently charged or charged due to the pH of the system) may promote an electrophoretic mechanism when associated with microbial membranes, which may promote the lysis of the microbe. Any such covalently bonded quaternary ammonium cation polymeric coatings may be used to give an antimicrobial property to the tongue scraper surface.

Antimicrobial coatings may be covalently attached to the surface by a variety of methods and may include, for example, creating suitable reaction sites, such as free hydroxyl or amino groups, by coronal discharge, surface etching, hydrolyzation or other methods that disrupt the surface of the tongue scraper to create sites of suitable reactivity. The antimicrobial coatings may then be synthesized by reacting the various precursors with the prepared surface of the tongue scraper to build the proper coating. In other cases, silanes may be used as coupling agents to complex antimicrobial moeties to the tongue scraper.

In yet further embodiments, antimicrobial activity may be achieved by utilizing the antimicrobial properties of various metals, especially transition metals which have little to no effect on humans. Examples may include sources of free silver ions, which are noted for their antimicrobial effects and few biological effects on humans. Metal ion antimicrobial activity may be created by a variety of methods that may include, for example, mixing a source of a metal ion with the polymer of the tongue scraper during manufacture, coating the surface by methods such as plasma deposition, loosely complexing the metal ion source by disrupting the surface of the tongue scraper to form affinity or binding sites by methods such as etching or coronal discharge, and depositing a metal onto the surface by means such as electroplating, photoreduction and precipitation. The tongue scraper may then slowly release free metal ions during use that may produce an antimicrobial effect.

In still further embodiments, the tongue scraper may be coated with a de-sensitizing agent, for example. The desensitizing agents may include alkali metal salt including a potassium salt, a sodium salt, a lithium salt or mixtures thereof, including alkali nitrates such as potassium nitrate, sodium nitrate and lithium nitrate, and other potassium salts such as potassium chloride, potassium citrate and potassium bicarbonate; or alkaline metal salts including calcium salts and strontium salts. The salt is, for example, water soluble or at least sparingly water soluble, and the appropriate anions may be chosen to facilitate in their solubility. For example, the appropriate anions may include chlorides, carbonates, nitrates, saccharins, phosphates or mixtures thereof. For example, the alkali metal salt may include at least one potassium salt, or sodium salt, and more for example, potassium nitrate, sodium nitrate, potassium chloride, potassium bicarbonate or sodium saccharin.

In other embodiments, the tongue scraper 11 may include both antimicrobial agents that are coated onto the tongue scraper 11 as a means of dispensing them onto the tongue and covalently bonded ones for helping to reduced microbial growth on the tongue scraper 11.

The coating may be present over substantially the entire exposed surfaces of the tongue scraper 11, or it may be present only on the surfaces that come into contact with the tongue. In the embodiments where the coating is only present on the surfaces that come into contact with the tongue, the surfaces may be roughened to hide the material inside the valleys or pits, as noted above.

In other embodiments, the bristles of the tooth brush may also be coated or treated with any of the various medicaments or coatings discussed above. This may give further therapeutic effect to the tooth brush. Other coatings including amorphous calcium or strontium compounds suitable for remineralizing as well as de-sensitizing may be used. Amorphous calcium compounds such as amorphous calcium phosphate (ACP), amorphous calcium phosphate fluoride (ACPF), amorphous calcium carbonate phosphate (ACCP), amorphous calcium carbonate phosphate (ACCP), and amorphous calcium carbonate phosphate fluoride (ACCPF) may be used as a sensitivity relief agent alone or in combination with alkali metal salts. These amorphous compounds are disclosed in U.S. Pat. Nos. 5,037,639, 5,268,167, 5,437,857, 5,562,895, 6,000,341, and 6,056,930, the disclosure of each is hereby incorporated by reference in its entirety.

Amorphous strontium compounds such as amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF) and amorphous strontium calcium carbonate phosphate fluoride (ASCCPF), such as disclosed in U.S. Pat. No. 5,534,244 may be used, the content of which is hereby incorporated by reference in its entirety.

The amorphous compounds are generally present separately, for example, a first component may include a source of phosphate and a second component may include a source of calcium or strontium. When the two components are mixed, the source of phosphate and the source of calcium, strontium or mixture may combine to form amorphous calcium phosphate, which when applied to teeth, may precipitate onto the surface of the teeth where it may be incorporated into hydroxyapatite, assisting in remineralization of the tooth enamel, as well as decreasing sensitivity. Thus, these alkaline metal salts also have the added advantage of being used in remineralization. Any method of keeping these sources separate prior to use may be used, such as separate dispensers for dispensing a coating onto the tooth brush prior to use.

Having described the present invention in reference to the embodiments mentioned above, it will be understood that any variations and equivalents are within the scope of the present invention.

The invention claimed is:

1. A dental apparatus comprising:
 a substantially longitudinal housing having a substantially hollow interior, a distal end, a proximal end, vents along at least one portion of the housing; and
 a tongue scraper fixedly mounted inside the housing by means of an extensible spring.

2. The dental apparatus of claim 1 wherein said tongue scraper is adapted to be pulled out of the housing as an extension of the housing or in a perpendicular direction to the substantially longitudinal housing.

3. The dental apparatus of claim 1 wherein said housing further comprises a longitudinal opening along at least a portion of the housing or an opening in at least a portion of the housing.

4. The dental apparatus of claim 3 wherein said opening is fitted with a door.

5. The dental apparatus of claim 1 wherein said apparatus comprises an electric tooth brush.

6. The dental apparatus of claim 1 wherein said tooth brush further comprises a light source.

7. A dental apparatus comprising:
a substantially longitudinal housing having a substantially hollow interior, a distal end, a proximal end; and
a tongue scraper mounted inside the housing; wherein said tongue scraper comprises a coating.

8. The dental apparatus of claim 7 wherein said tongue scraper is fully extended and slidably mounted inside the housing during storage.

9. The dental apparatus of claim 7 wherein said tongue scraper is present in roll form inside the housing.

10. The dental apparatus of claim 9 wherein the housing comprises tracks along its interior.

11. The dental apparatus of claim 10 wherein the roll is adapted to slide along the track.

12. The dental apparatus of claim 9 wherein the roll is fixedly or slidably mounted in the housing.

13. The dental apparatus of claim 7 wherein said housing comprises two separate portions slidably attached to one another.

14. The dental apparatus of claim 7 wherein said coating comprises therapeutic agents.

15. The dental apparatus of claim 14 wherein said therapeutic agents comprises antimicrobial agents, de-sensitizing agents, medicament or mixtures thereof.

16. A dental apparatus comprising:
a substantially longitudinal housing having a substantially hollow interior, a distal end, a proximal end, and a tooth brush at its proximal end; and a tongue scraper in roll form mounted inside the housing.

17. The dental apparatus of claim 16 wherein the roll is fixedly or slidably mounted to the housing.

18. The dental apparatus of claim 16 wherein the housing comprises tracks along its interior.

19. The dental apparatus of claim 16 wherein the roll is adapted to slide along the track.

20. The dental apparatus of claim 16 wherein said housing further comprises an opening in at least a portion of the housing.

21. The dental apparatus of claim 20 wherein said opening is fitted with a door.

22. The dental apparatus of claim 16 wherein said housing comprises two separate portions slidably attached to each other.

23. The dental apparatus of claim 16 wherein said housing further comprises vents.

24. The dental apparatus of claim 16 wherein said apparatus is an electric tooth brush.

25. The dental apparatus of claim 16 wherein said tongue scraper comprises a coating comprising therapeutic agents.

26. The dental apparatus of claim 25 wherein said therapeutic agents comprises antimicrobial agents, de-sensitizing agents, medicament or mixtures thereof.

27. A dental apparatus comprising:
a substantially longitudinal housing having a distal end, a proximal end, and a tooth brush at its proximal end; and
a tongue scraper mounted along the outside of the housing; wherein said tongue scraper is slidably attached to both ends of the housing.

28. The dental apparatus of claim 27 wherein said tooth brush is an electric tooth brush.

29. The dental apparatus of claim 27 wherein said tooth brush further comprises a light source.

30. The dental apparatus of claim 27 wherein said tongue scraper comprises a coating comprising therapeutic agents.

31. The dental apparatus of claim 30 wherein said therapeutic agents comprises antimicrobial agents, de-sensitizing agents, medicament or mixtures thereof.

32. A dental apparatus comprising:
a substantially longitudinal housing having two separate portions slidably attached to each other;
a tooth brush attached to at least one portion of the housing; and
a tongue scraper mounted inside the housing; wherein the two portions are telescopically attached and said tongue scraper is exposed when said portions are collapsed.

33. The dental apparatus of claim 32 wherein said tooth brush is an electric tooth brush.

34. The dental apparatus of claim 32 wherein said tongue scraper comprises a coating comprising therapeutic agents.

35. The dental apparatus of claim 34 wherein said housing further comprises vents along at least part of at least one portion of the housing.

36. The dental apparatus of claim 34 wherein said therapeutic agents comprises antimicrobial agents, de-sensitizing agents, medicament or mixtures thereof.

* * * * *